(12) United States Patent
Brunner-Schwarz et al.

(10) Patent No.: US 7,713,930 B2
(45) Date of Patent: *May 11, 2010

(54) ACIDIC INSULIN PREPARATIONS HAVING IMPROVED STABILITY

(75) Inventors: Anette Brunner-Schwarz, Frankfurt (DE); Norbert Lill, Kronberg (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 12/328,208

(22) Filed: Dec. 4, 2008

(65) Prior Publication Data

US 2009/0082255 A1  Mar. 26, 2009

Related U.S. Application Data

(63) Continuation of application No. 11/089,777, filed on Mar. 25, 2005, now Pat. No. 7,476,652, which is a continuation of application No. 10/461,740, filed on Jun. 13, 2003, now abandoned.

(60) Provisional application No. 60/409,338, filed on Sep. 9, 2002.

(30) Foreign Application Priority Data

Jun. 18, 2002 (DE) .................................. 10227232

(51) Int. Cl.
A61K 38/28 (2006.01)
(52) U.S. Cl. ........................................................ 514/3
(58) Field of Classification Search .................. None
See application file for complete search history.

(56) References Cited

U.S. PATENT DOCUMENTS

| | | | |
|---|---|---|---|
| 3,758,683 A | 9/1973 | Jackson | |
| 3,868,358 A | 2/1975 | Jackson | |
| 4,153,689 A | 5/1979 | Hirai et al. | |
| 4,608,364 A | 8/1986 | Grau | |
| 4,614,730 A | 9/1986 | Hansen et al. | |
| 4,644,057 A | 2/1987 | Bicker et al. | |
| 4,701,440 A | 10/1987 | Grau | |
| 4,731,405 A | 3/1988 | Kirsch et al. | |
| 4,783,441 A | 11/1988 | Thurow | |
| 4,839,341 A | 6/1989 | Massey et al. | |
| 4,885,164 A | 12/1989 | Thurow | |
| 4,959,351 A | 9/1990 | Grau | |
| 4,994,439 A | 2/1991 | Longenecker et al. | |
| 5,008,241 A | 4/1991 | Markussen et al. | |
| 5,034,415 A | 7/1991 | Rubin | |
| 5,101,013 A | 3/1992 | Dorschug et al. | |
| 5,177,058 A | 1/1993 | Dorschug | |
| 5,358,857 A | 10/1994 | Stengelin et al. | |
| 5,397,771 A | 3/1995 | Bechgaard et al. | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,496,924 A | 3/1996 | Habermann et al. | |
| 5,506,203 A | 4/1996 | Backstrom et al. | |
| 5,514,656 A | 5/1996 | Chance et al. | |
| 5,534,488 A | 7/1996 | Hoffmann | |
| 5,547,929 A | 8/1996 | Anderson, Jr. et al. | |
| 5,559,094 A | 9/1996 | Brems et al. | |
| 5,597,796 A | 1/1997 | Brange | |
| 5,614,219 A | 3/1997 | Wunderlich et al. | |
| 5,656,722 A * | 8/1997 | Dorschug .................. 530/303 |
| 5,663,291 A | 9/1997 | Obermeier et al. | |
| 5,693,608 A | 12/1997 | Bechgaard et al. | |
| 5,700,662 A | 12/1997 | Chance et al. | |
| 5,707,641 A | 1/1998 | Gertner et al. | |
| 5,783,556 A | 7/1998 | Clark et al. | |
| 5,824,638 A | 10/1998 | Burnside et al. | |
| 5,948,751 A | 9/1999 | Kimer et al. | |
| 5,985,309 A | 11/1999 | Edwards et al. | |
| 6,034,054 A | 3/2000 | DeFelippis et al. | |
| 6,043,214 A | 3/2000 | Jensen et al. | |
| 6,051,551 A | 4/2000 | Hughes et al. | |
| 6,100,376 A | 8/2000 | Doerschug et al. | |
| 6,174,856 B1 | 1/2001 | Langballe et al. | |
| 6,211,144 B1 | 4/2001 | Havelund | |
| 6,248,363 B1 | 6/2001 | Patel et al. | |

(Continued)

FOREIGN PATENT DOCUMENTS

| | | | |
|---|---|---|---|
| AU | 62066/86 | | 3/1987 |
| AU | 75916/87 | | 1/1988 |
| CA | 1173388 | | 8/1984 |
| CA | 1258427 | * | 8/1989 |
| CA | 1336329 | | 7/1995 |
| CA | 1341203 | | 3/2001 |
| EP | 0 166 529 | | 1/1986 |
| EP | 0 180 920 | | 5/1986 |
| EP | 0 194 864 | | 9/1986 |
| EP | 0 200 383 | | 12/1986 |
| EP | 0 224 885 A1 | | 6/1987 |
| EP | 0 254 516 | | 1/1988 |
| EP | 0 383 472 | | 8/1990 |
| EP | 0419504 | | 1/1994 |
| EP | 0214826 | | 10/1994 |

(Continued)

OTHER PUBLICATIONS

Brange, et al., Toward Understanding Insulin Fibrillation, Journal of Pharmaceutical Sciences, 86:517-525 (1997).

(Continued)

*Primary Examiner*—Christopher R. Tate
*Assistant Examiner*—Roy Teller
(74) *Attorney, Agent, or Firm*—Balaram Gupta

(57) ABSTRACT

The invention relates to a pharmaceutical formulation comprising a polypeptide selected from the group consisting of insulin, an insulin metabolite, an insulin analog, an insulin derivative and combinations thereof; a surfactant or combinations of two or more surfactants; optionally a preservative or combinations of two or more preservatives; and optionally an isotonicizing agent, buffers or further excipients or combinations thereof, the pharmaceutical formulation having a pH in the acidic range.

20 Claims, No Drawings

U.S. PATENT DOCUMENTS

| | | | |
|---|---|---|---|
| 6,267,981 | B1 | 7/2001 | Okamoto et al. |
| 6,309,663 | B1 | 10/2001 | Patel et al. |
| 6,310,038 | B1 | 10/2001 | Havelund |
| 6,335,316 | B1 | 1/2002 | Hughes et al. |
| 6,468,959 | B1 | 10/2002 | Wunderlich et al. |
| 6,489,292 | B1 | 12/2002 | Havelund et al. |
| 6,734,162 | B2 | 5/2004 | Van Antwerp et al. |
| 6,818,738 | B2 | 11/2004 | Havelund |
| 6,908,897 | B2 | 6/2005 | Brandenburg et al. |
| 6,960,561 | B2 | 11/2005 | Boderke et al. |
| 7,205,276 | B2 | 4/2007 | Boderke |
| 7,205,277 | B2 | 4/2007 | Boderke |
| 7,476,652 | B2 * | 1/2009 | Brunner-Schwarz et al. ... 514/3 |
| 2001/0033868 | A1 | 10/2001 | Rossling et al. |
| 2001/0039260 | A1 | 11/2001 | Havelund |
| 2002/0107265 | A1 | 8/2002 | Chen et al. |
| 2002/0198140 | A1 | 12/2002 | Havelund |
| 2003/0004096 | A1 | 1/2003 | Boderke et al. |
| 2004/0097410 | A1 | 5/2004 | Zheng et al. |
| 2007/0155653 | A1 | 7/2007 | Boderke |

FOREIGN PATENT DOCUMENTS

| | | |
|---|---|---|
| EP | 0678522 | 10/1995 |
| EP | 0 837 072 | 4/1998 |
| EP | 0846265 | 6/1998 |
| EP | 0375437 | 9/1998 |
| EP | 1 172 114 | 1/2002 |
| FR | 2456522 | 12/1980 |
| GB | 1527605 | 10/1978 |
| GB | 1554157 | 10/1979 |
| WO | WO 83/00288 | 2/1983 |
| WO | WO 88/06599 | 9/1988 |
| WO | WO 90/07522 | 7/1990 |
| WO | WO 91/16929 | 11/1991 |
| WO | WO 92/00321 | 1/1992 |
| WO | WO 94/14461 | 7/1994 |
| WO | WO 96/04307 | 2/1996 |
| WO | WO 96/07399 | 3/1996 |
| WO | WO 96/11705 | 4/1996 |
| WO | WO 96/41606 | 12/1996 |
| WO | WO 97/01331 | 1/1997 |
| WO | WO 98/42749 | 10/1998 |
| WO | WO 98/56406 | 12/1998 |
| WO | WO 99/24071 | 5/1999 |
| WO | WO 00/23098 | 4/2000 |
| WO | WO 00/23099 | 4/2000 |
| WO | WO 00/29013 | 5/2000 |
| WO | WO 00/74736 | 12/2000 |
| WO | WO 01/00223 | 1/2001 |
| WO | WO 01/12155 | 2/2001 |
| WO | WO 01/21154 | 3/2001 |
| WO | WO 01/28555 | 4/2001 |
| WO | WO 01/37808 | 5/2001 |
| WO | WO 01/43762 | 6/2001 |
| WO | WO 01/52937 | 7/2001 |
| WO | WO 01/93837 | 12/2001 |
| WO | WO 02/064115 | 8/2002 |
| WO | WO 02/076495 | 10/2002 |
| WO | WO 03/035028 | 5/2003 |
| WO | WO 03/035051 | 5/2003 |

OTHER PUBLICATIONS

Schubert-Zsilavecz, et al., Insulin Glargin Ein Langwirksames Insulinanalogon, Pharmazie 2:125-130 (2001).

Sluzky, et al., Kinetics of Insulin Aggregation in Aqueous Solutions Upon Agitation In The Presence of Hydrophobic Surfaces, Proc. Natl. Acad. Sci. USA. vol. 88, pp. 9377-9381, Nov. 1991.

The Diabetes Control and Complications Trial Research Group, The Effect Of Intensive Treatment of Diabetes On The Development And Progression Of Long-Term Complications In Insulin-Dependent Diabetes Mellitus, The New England Journal of Medicine, 329, 977-986 (1993).

Aoki, K, et al., Hydrolysis of Nonionic Surfactants, Ann. Rept. Takeda Res. Lab. 27, 172-176 (1968).

Garriques, L. N., et. al., The Effect of Mutations on the Structure of Insulin Fibrils Studied by Fourier Transform Infrared (FTIR) Spectroscopy and Electron Microscopy, Journal of Pharmaceutical Sciences, vol. 91, No. 12, (2002), pp. 2473-2480.

Whittingham, J. L., et. al., Insulin at PH2: Structure Analysis of the Conditions Promoting Insulin Fibre Formation, J. Mol. Biol., (2002), vol. 318, pp. 479-480.

Thurow and Geisen, "Stabilisation of dissolved proteins against denaturation at hydrophobic interfaces," Diabetologia, 27: 212-18 (1984).

Hinds et al., "Synthesis and Characterization of Poly(ethylene-glycol)-Insulin Conjugates," 2000, vol. 11, pp. 195-201.

Brange and Langkjaer, "Chemical stability of insulin—3. Influence of excipients, formulation and pH," Acta Pharm. Nord., 1992, 4(3): 149-158.

Brange et al. "Neutral insulin solutions physically stabilized by addition of Zn2+," Diabetic Medicine, 1986, pp. 532-536.

Lougheed et al. "Physical Stability of Insulin Formulations," Diabetes, 1983, 32: 424-32.

Kadima "Role of Metal Ions in the T- to R-Allosteric Transition in the Insulin Hexamer," Biochem. 38(41), 1999, p. 13443.

Nettleton et al. "Characterization of the Oligomeric States of Insulin in Self-Assembly and Amyloid Fibril Formation by Mass Spectrometry," Biophysical J., v79, 2000, p. 1053-1065.

Bakaysa et al., "Physicochemical basis for the rapid time-action of LysB28ProB29-insulin: Dissociation of a protein-ligand complex," Protein Science,1996, 5:2521-31.

Beintema and Campagne, "Molecular Evolution of Rodent Insulins," Mol. Biol. Evol. 4(1): 10-18, 1987.

Berger, "Towards more physiological insulin therapy in the 1990s—A comment," Diabetes Research and Clinical Practice, 6(1989), pp. S25-S31.

Bolli, "The pharmacokinetic basis of insulin therapy in diabetes mellitus," Diabetes Research and Clinical Practice, 9(1989), pp. S3-S16.

Brange et al., "Monomeric insulins and their experimental and clinical implications," Diabetes Care, 13(9): 923-45 (1990).

Brange, "Galenics of Insulin" 1987, p. 35-36.

Burgermeister et al. "D: The Isolation of Insulin from the Pancreas," Insulin, Part 2, 1975, p. 715-727.

Burke et al., "Nature of the B10 amino acid residue," Int. J. Peptide Protein Res., 23, 1984, p. 394-401.

Dixon et al., "Regeneration of Insulin Activity From the Separated and Inactive A and B Chains," Nature, vol. 188, No. 4752 (1960), pp. 721-724.

Drury et al., "Diabetic nephropathy," British Medical Bulletin, vol. 45, No. 1, 1989, pp. 127-147.

EP Search Report for Application 98110889.7-2105, Oct. 14, 1998.

Geiger, Chem. Zeitung, 100(3), p. 54-56.

German Search Report for Application 19726167.1, Nov. 24, 1997.

Home et al., "Insulin treatment: a decade of change," British Medical Bulletin, 1989, vol. 45, No. 1, pp. 92-110.

Kang et al., "Subcutaneous Insulin Absorption Explained by Insulin's Physicochemical Properties-Evidence from Absorption Studies of Soluble Human Insulin and Insulin Analogues in Humans," Diabetes Care, vol. 14, No. 11, 1991, pp. 942-948.

Kemmler et al., "Studies on the Conversion of Proinsulin to Insulin," The Journal of Biological Chemistry, vol. 246, No. 22, 1971, pp. 6786-6791.

Kohner, "Diabetic retinopathy," British Medical Bulletin, vol. 45, No. 1, 1989, pp. 148-173.

Markussen et al., "Soluble, prolonged-acting insulin derivatives. I. Degree of protraction and crystallizability of insulins substituted in the termini of the B-chain," Prot. Eng. 1(3), 1987, p. 205-213.

Markussen et al., "Soluble, prolonged-acting insulin derivatives. II. Degree of protraction and crystallizability of insulins substituted in positions A17, B8, B13, B27 and B30," Prot. Eng. 1(3), 1987, p. 215-223.

Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, p. 157-166.

Müller et al., "Insulin Signaling in the Yeast Saccharomyces cerevisiae—1. Stimulation of Glucose Metabolism and Snf 1 Kinase by Human Insulin," Biochemistry, vol. 37, No. 24, 1998, pp. 8683-8695.

Pillion et al., "Dodecylmaltoside-mediated Nasal and Ocular Absorption of Lyspro-Insulin: Independence of Surfactant from Multimer Dissociation," Pharmaceutical Research, vol. 15, No. 10, 1998, pp. 1637-1639.

Schartz et al., "A superactive insulin: [B10-Aspartic acid]insulin(human)," Proc. Natl. Acad. Sci. USA, v84, 1987, pp. 6408-6411.

Sundby, "Separation and Characterization of Acid-Induced Insulin Transformation Products by Paper Electrophoresis in 7 M Urea," J. Biol. Chem. 237(11), 1962, p. 3406-3411.

Volund et al., "In Vitro and In Vivo Potency of Insulin Analogues Designed for Clinical Use," Diab. Med. 8, 1991, p. 839-847.

Ward, "Diabetic neuropathy," British Medical Bulletin, vol. 45, No. 1, 1989, pp. 111-126.

Zinman, "The Physiologic Replacement of Insulin," The New England J. Med. 321(6), 1989, p. 363-370.

* cited by examiner

US 7,713,930 B2

ACIDIC INSULIN PREPARATIONS HAVING IMPROVED STABILITY

This application is a continuation of U.S. application Ser. No. 11/089,777, filed Mar. 25, 2005, now allowed, which is a continuation of Ser. No. 10/461,740, filed Jun. 13, 2003, now abandoned; both of which are incorporated herein by reference in their entirety which claims the benefit of U.S. Provisional Application No. 60/409,338, filed Sep. 9, 2002, and Federal Republic of Germany Application 10227232.8, filed Jun. 18, 2002.

SUMMARY OF THE INVENTION

The invention relates to a pharmaceutical formulation comprising a polypeptide selected from the group consisting of insulin, an insulin metabolite, an insulin analog, an insulin derivative or combinations thereof; a surfactant or combinations of two or more surfactants; optionally a preservative or combinations of two or more preservatives; and optionally an isotonicizing agent, buffers or further excipients or combinations thereof, the pharmaceutical formulation having a pH in the acidic range. These formulations can be employed for the treatment of diabetes, and are particularly suitable for preparations in which a high stability to thermal and/or physico-mechanical stress is necessary. The invention likewise relates to parenteral preparations which contain such formulations and can be used in diabetes and to methods for producing the preparations and for improving the stability of insulin preparations.

BACKGROUND OF THE INVENTION

Worldwide, approximately 120 million people suffer from diabetes mellitus. Among these, approximately 12 million are type I diabetics, for whom the substitution of the lacking endocrine insulin secretion is the only currently possible therapy. The affected persons are dependent lifelong on insulin injections, as a rule a number of times daily. In contrast to type I diabetes, there is not basically a deficiency of insulin in type II diabetes, but in a large number of cases, especially in the advanced stage, treatment with insulin, optionally in combination with an oral antidiabetic, is regarded as the most favorable form of therapy.

In the healthy person, the release of insulin by the pancreas is strictly coupled to the concentration of blood glucose. Elevated blood glucose levels, such as occur after meals, are rapidly compensated by a corresponding increase in insulin secretion. In the fasting state, the plasma insulin level falls to a basal value which is adequate to guarantee a continuous supply of insulin-sensitive organs and tissue with glucose and to keep hepatic glucose production low at night. The replacement of endogenous insulin secretion by exogenous, mostly subcutaneous administration of insulin, as a rule does not approximate the quality of the physiological regulation of the blood glucose described above. Often, deviations of blood glucose upward or downward occur, which in their severest forms can be life-threatening. In addition, however, blood glucose levels which are increased for years without initial symptoms are a considerable health risk. The large-scale DCCT study in the USA (The Diabetes Control and Complications Trial Research Group (1993) N. Engl. J. Med. 329, 977-986) demonstrated clearly that chronically elevated blood glucose levels are essentially responsible for the development of diabetic late damage. Diabetic late damage is microvascular and macrovascular damage which is manifested, under certain circumstances, as retinopathy, nephropathy or neuropathy and leads to loss of sight, kidney failure and the loss of extremities and is moreover accompanied by an increased risk of cardiovascular diseases. In view of this, an improved therapy of diabetes should be aimed at keeping the blood glucose as closely as possible in the physiological range. According to the concept of intensified insulin therapy, this should be achieved by repeated daily injections of rapid- and slow-acting insulin preparations. Rapid-acting formulations are given at meals in order to level out the postprandial increase in the blood glucose. Slow-acting basal insulins should ensure the basic supply with insulin, in particular during the night, without leading to hypoglycemia.

Insulin is a polypeptide of 51 amino acids, which are divided into 2 amino acid chains: the A chain having 21 amino acids and the B chain having 30 amino acids. The chains are connected to one another by means of 2 disulfide bridges. Insulin preparations have been employed for diabetes therapy for many years. Not only are naturally occurring insulins used, but recently also insulin derivatives and analogs.

Insulin analogs are analogs of naturally occurring insulins, namely human insulin or animal insulins, which differ by substitution of at least one naturally occurring amino acid residue with other amino acids and/or addition/removal of at least one amino acid residue from the corresponding, otherwise identical, naturally occurring insulin. The amino acids can in this case also be those which do not occur naturally.

Insulin derivatives are derivatives of naturally occurring insulin or an insulin analog which are obtained by chemical modification. This chemical modification can consist, for example, of the addition of one or more specific chemical groups to one or more amino acids. As a rule, insulin derivatives and insulin analogs have a somewhat modified action compared with human insulin.

Insulin analogs having an accelerated onset of action are described in EP 0 214 826, EP 0 375 437 and EP 0 678 522. EP 0 124 826 relates, inter alia, to substitutions of B27 and B28. EP 0 678 522 describes insulin analogs which in position B29 have various amino acids, preferably proline, but not glutamic acid.

EP 0 375 437 includes insulin analogs with lysine or arginine in B28, which can optionally be additionally modified in B3 and/or A21.

In EP 0 419 504, insulin analogs are disclosed which are protected against chemical modifications, in which asparagine in B3 and at least one further amino acid in the positions A5, A15, A18 or A21 are modified.

In WO 92/00321, insulin analogs are described in which at least one amino acid of the positions B1-B6 is replaced by lysine or arginine. According to WO 92/00321, insulins of this type have a prolonged action. The insulin analogs described in EP-A 0 368 187 also have a delayed action.

The insulin preparations of naturally occurring insulins on the market for insulin substitution differ in the origin of the insulin (e.g. bovine, porcine, human insulin), and also the composition, whereby the profile of action (onset of action and duration of action) can be influenced. By combination of various insulin preparations, very different profiles of action can be obtained and blood sugar values which are as physiological as possible can be established. Recombinant DNA technology today makes possible the preparation of such modified insulins. These include insulin glargine (Gly(A21)-Arg(B31)-Arg(B32)-human insulin) with a prolonged duration of action. Insulin glargine is injected as an acidic, clear solution and precipitates on account of its solution properties in the physiological pH range of the subcutaneous tissue as a stable hexamer associate. Insulin glargine is injected once daily and is distinguished compared with other long-acting insulins by its flat serum profile and the reduction of the danger of nightly hypoglycemia associated therewith (Schubert-Zsilavecz et al., 2:125-130(2001)).

The specific preparation of insulin glargine, which leads to the prolonged duration of action, is characterized, in contrast to previously described preparations, by a clear solution having an acidic pH. Especially at acidic pH, insulins, however, show a decreased stability and an increased proneness to aggregation on thermal and physicomechanical stress, which can make itself felt in the form of turbidity and precipitation (particle formation) (Brange et al., J. Ph. Sci 86:517-525 (1997)).

The proneness to aggregation can additionally be promoted by hydrophobic surfaces which are in contact with the solution (Sluzky et al., Proc. Natl. Acad. Sci. 88:9377-9381 (1991). Surfaces which can be considered as hydrophobic are the glass vessels of the preparations, the stopper material of the sealing caps or the boundary surface of the solution with the air supernatant. In addition, very fine silicone oil droplets can function as additional hydrophobic aggregation nuclei in the taking of the daily insulin dose by means of customary, siliconized insulin syringes and accelerate the process.

WO 01/43762 describes aqueous, parenteral pharmaceutical preparations comprising a polypeptide and glycerol, in which the stabilization of the preparation is to be achieved by purifying off destabilizing constituents of the glycerol.

WO 00/23098 describes insulin preparations stabilized using polysorbate 20 or poloxamer 188 for pulmonary administration, but does not describe the stabilization in an acidic solution against aggregation nuclei.

WO 02/076495 describes zinc-free and low-zinc insulin preparations having improved stability at room and body temperature and to mechanical stress by the addition of surfactants, but does not describe the stabilization of acidic insulin preparations against hydrophobic aggregation nuclei.

The present invention was thus based on the object of finding preparations for acid-soluble insulins containing surfactants, which are distinguished by a high long-term stability to stress due to temperature or physicomechanical stressing and tolerate a high stress with hydrophobic aggregation nuclei.

DETAILED DESCRIPTION OF THE INVENTION

It has now surprisingly been found that the addition of surfactants can greatly increase the stability of acidic insulin preparations and thus preparations can be produced which guarantee superior stability to hydrophobic aggregation nuclei for several months under temperature stress.

The pharmaceutical preparations of the present invention contain 60-6000 nmol/ml, preferably 240-3000 nmol/ml, of an insulin, an insulin metabolite, an insulin analog or an insulin derivative.

The surfactants which can be used are, inter alia, nonionic surfactants. In particular, pharmaceutically customary surfactants are preferred, such as, for example: partial and fatty acid esters and ethers of polyhydric alcohols such as of glycerol, sorbitol and the like (SPAN®, TWEEN®, in particular TWEEN® 20 and TWEEN® 80, MYRJ®, BRIJ®), CREMOPHOR® or poloxamers. The surfactants are present in the pharmaceutical composition in a concentration of 5-200 µg/ml, preferably of 5-120 µg/ml and particularly preferably of 20-75 µg/ml.

The preparation can additionally optionally contain preservatives (e.g. phenol, cresol, parabens), isotonicizing agents (e.g. mannitol, sorbitol, lactose, dextrose, trehalose, sodium chloride, glycerol), buffer substances, salts, acids and alkalis and also further excipients. These substances can in each case be present individually or alternatively as mixtures.

Glycerol, dextrose, lactose, sorbitol and mannitol are customarily present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, preferably 10-100 mM. Further excipients can be, inter alia, salts or arginine.

The invention therefore relates to a pharmaceutical formulation comprising a polypeptide selected from the group consisting of insulin, an insulin analog, an insulin derivative, an active insulin metabolite and combinations thereof; a surfactant or combinations of two or more surfactants; optionally a preservative or combinations of two or more preservatives; and optionally an isotonicizing agent, buffer substances and/or further excipients or combinations thereof, the pharmaceutical formulation being a clear solution which has a pH in the acidic range (pH 1-6.8), preferably pH 3.5-6.8, very particularly preferably 3.5-4.5.

Preferred pharmaceutical formulations of the present invention are those wherein the surfactant is selected from the group consisting of partial and fatty acid esters and ethers of polyhydric alcohols such as of glycerol and sorbitol, and polyols; the partial and fatty acid esters and ethers of glycerol and sorbitol being selected from the group consisting of SPAN®, TWEEN®, MYRJ®, BRIJ®, CREMOPHOR®; the polyols being selected from the group consisting of polypropylene glycols, polyethylene glycols, poloxamers, PLURONICS®, and TETRONICS®; the preservative being selected from the group consisting of phenol, cresol, and parabens; the isotonicizing agent being selected from the group consisting of mannitol, sorbitol, sodium chloride, and glycerol; the excipients being selected from the group consisting of buffer substances, acids, and alkalis; the insulin analog being selected from the group consisting of Gly(A21)-Arg(B31)-Arg(B32)-human insulin; Lys(B3)-Glu(B29)-human insulin; Lys$^{B28}$Pro$^{B29}$ human insulin, B28 Asp-human insulin, human insulin in which proline in position B28 has been substituted by Asp, Lys, Leu, Val or Ala and where in position B29 Lys can be substituted by Pro; AlaB26-human insulin; des(B28-B30)-human insulin; des(B27)-human insulin and des(B30)-human insulin; the insulin derivative being selected from the group consisting of B29-N-myristoyl-des(B30) human insulin, B29-N-palmitoyl-des(B30) human insulin, B29-N-myristoyl human insulin, B29-N-palmitoyl human insulin, B28-N-myristoyl Lys$^{B28}$Pro$^{B29}$ human insulin, B28-N-palmitoyl-Lys$^{B28}$Pro$^{B29}$ human insulin, B30-N-myristoyl-Thr$^{B29}$Lys$^{B30}$ human insulin, B30-N-palmitoyl-Thr$^{B29}$Lys$^{B30}$ human insulin, B29-N-(N-palmitoyl-γ-glutamyl)-des(B30) human insulin, B29-N-(N-lithocholyl-γ-glutamyl)-des(B30) human insulin, B29-N-(ω-carboxyheptadecanoyl)-des(B30) human insulin and B29-N-(ω-carboxyheptadecanoyl) human insulin.

A further subject of the invention is a pharmaceutical formulation such as described above, in which the insulin, the insulin analog, the active insulin metabolite and/or the insulin derivative is present in a concentration of 60-6000 nmol/ml, preferably in a concentration of 240-3000 nmol/ml (this corresponds approximately to a concentration of 1.4-35 mg/ml or 40-500 units/ml);

in which the surfactant is present in a concentration of 5-200 µg/ml, preferably of 5-120 µg/ml and particularly preferably of 20-75 µg/ml.

A further subject of the invention is a pharmaceutical formulation such as mentioned above, in which glycerol and/or mannitol is present in a concentration of 100-250 mM, and/or NaCl is preferably present in a concentration of up to 150 mM.

A further subject of the invention is a pharmaceutical formulation such as mentioned above, in which a buffer substance is present in a concentration of 5-250 mM.

A further subject of the invention is a pharmaceutical insulin formulation which contains further additives such as, for example, salts which delay the release of insulin. Mixtures of such delayed-release insulins with formulations described above are included therein.

A further subject of the invention is a method for the production of such pharmaceutical formulations. Likewise, a further subject of the invention is the use of such formulations for the treatment of diabetes mellitus.

A further subject of the invention is the use or the addition of surfactants as stabilizer during the process for the production of insulin, insulin analogs or insulin derivatives or their preparations.

EXAMPLES

The following examples illustrate, but by no means limit, the present invention.

Comparison investigations: Different preparations containing the insulin analog insulin glargine (Gly(A21), Arg(B31), Arg(B32)-human insulin) are prepared. To this end, insulin glargine is suspended in one part of water for injection, dissolved at pH 3-4, the other constituents are added, the pH is adjusted to 4.0+/−0.2 using hydrochloric acid/NaOH and the mixture is made up to the final volume. The concentration of insulin glargine in each of the experiments described below is 3.6378 mg/ml (corresponds to 100 units/ml). A second preparation is produced identically, but a specific amount of a surfactant is additionally added. The solutions are filled into 10 ml glass vessels (vials) and fitted with crimp caps. These vessels are now exposed to simulated in use or physicomechanical stress conditions:

1. In use test: The vessels are sorted into boxes with turned-up lids and stored during the investigation period of 28 days at +25° C. and controlled room humidity with exclusion of light. To simulate taking by the patient, once daily about 5 IU of the solutions are withdrawn using a customary insulin syringe and discarded. At the beginning and end of the working week this procedure is carried out twice in order to simulate taking at the weekend. Before each withdrawal, visual assessment of the solution in the vessels for turbidity and/or particle formation is carried out.
2. Shaking test: The vessels are placed in a box with a turned-up lid lying on a laboratory shaker having an incubator and thermostat and shaken at 25° C. with 90 movements/min parallel to the horizontal movement for a period of time of 10 days. After defined times, the turbidity value of the samples is determined by means of a laboratory turbidity photometer (nephelometer) in formaldazine nephelometric units (formaldazine nephelometric unit=FNU). The turbidity value corresponds to the intensity of the scattered radiation of the light incident on suspended particles in the sample.

Example 1

Stabilization of the in Use Period of Insulin Glargine Using Polysorbate 20 (Tween® 20)

a) The solution is sterile-filtered through a combination of 0.2 μm und 0.1 μm filters. It is then poured into 10 ml injection vials and sealed using crimp caps having an inserted sealing disk.

b) A comparison solution is prepared identically, but first a suitable amount of surfactant (10-30 ppm of polysorbate 20) is suspended in water for injection. The samples are stored at +5° C., 25° C. and 37° C. for a fixed period of time.

10 samples in each case are then subjected to an in use test. The results are shown in the table below.

Storage for 3 months at 5° C.

| Test sample | Number of vials with particle formation after | | | |
| --- | --- | --- | --- | --- |
| | 7 days | 14 days | 21 days | 28 days |
| Insulin glargine | 7 | 10 | 10 | 10 |
| Insulin glargine + 0.010 mg/ml of polysorbate 20 | 0 | 0 | 0 | 0 |
| Insulin glargine + 0.015 mg/ml of polysorbate 20 | 0 | 0 | 0 | 0 |
| Insulin glargine + 0.020 mg/ml of polysorbate 20 | 0 | 0 | 0 | 1 |
| Insulin glargine + 0.030 mg/ml of polysorbate 20 | 0 | 0 | 0 | 0 |

Storage for 6 months at 5° C.

| Test sample | Number of vials with particle formation after | | | |
| --- | --- | --- | --- | --- |
| | 7 days | 14 days | 21 days | 28 days |
| Insulin glargine | 1 | 10 | 10 | 10 |
| Insulin glargine + 0.010 mg/ml of polysorbate 20 | 0 | 0 | 0 | 1 |
| Insulin glargine + 0.015 mg/ml of polysorbate 20 | 0 | 0 | 0 | 0 |
| Insulin glargine + 0.020 mg/ml of polysorbate 20 | 0 | 0 | 0 | 1 |
| Insulin glargine + 0.030 mg/ml of polysorbate 20 | 0 | 0 | 1 | 0 |

Storage for 3 months at 25° C.

| Test sample | Number of vials with particle formation after | | | |
| --- | --- | --- | --- | --- |
| | 7 days | 14 days | 21 days | 28 days |
| Insulin glargine | 9 | 10 | 10 | 10 |
| Insulin glargine + 0.010 mg/ml of polysorbate 20 | 2 | 2 | 2 | 2 |

-continued

Storage for 6 months at 25° C.

| Test sample | Number of vials with particle formation after | | | |
|---|---|---|---|---|
| | 7 days | 14 days | 21 days | 28 days |
| Insulin glargine + 0.015 mg/ml of polysorbate 20 | 0 | 0 | 0 | 1 |
| Insulin glargine + 0.020 mg/ml of polysorbate 20 | 0 | 0 | 0 | 0 |
| Insulin glargine + 0.030 mg/ml of polysorbate 20 | 0 | 0 | 0 | 0 |

Storage for 1 month at 37° C.

| Test sample | Number of vials with particle formation after | | | |
|---|---|---|---|---|
| | 7 days | 14 days | 21 days | 28 days |
| Insulin glargine | 10 | 10 | 10 | 10 |
| Insulin glargine + 0.010 mg/ml of polysorbate 20 | 0 | 0 | 0 | 1 |
| Insulin glargine + 0.015 mg/ml of polysorbate 20 | 0 | 0 | 1 | 0 |
| Insulin glargine + 0.020 mg/ml of polysorbate 20 | 0 | 0 | 0 | 0 |
| Insulin glargine + 0.030 mg/ml of polysorbate 20 | 0 | 0 | 0 | 0 |

Storage for 3 months at 37° C.

| Test sample | Number of vials with particle formation after | | | |
|---|---|---|---|---|
| | 7 days | 14 days | 21 days | 28 days |
| Insulin glargine | 0 | 10 | 10 | 10 |
| Insulin glargine + 0.010 mg/ml of polysorbate 20 | 0 | 3 | 3 | 5 |
| Insulin glargine + 0.015 mg/ml of polysorbate 20 | 0 | 0 | 0 | 0 |
| Insulin glargine + 0.020 mg/ml of polysorbate 20 | 0 | 0 | 0 | 0 |
| Insulin glargine + 0.030 mg/ml of polysorbate 20 | 0 | 0 | 0 | 0 |

| Test sample | Number of vials with particle formation after | | | |
|---|---|---|---|---|
| | 7 days | 14 days | 21 days | 28 days |
| Insulin glargine | 5 | 9 | 10 | 10 |
| Insulin glargine + 0.010 mg/ml of polysorbate 20 | 1 | 1 | 1 | 1 |

-continued

Storage for 6 months at 37° C.

| Test sample | Number of vials with particle formation after | | | |
|---|---|---|---|---|
| | 7 days | 14 days | 21 days | 28 days |
| Insulin glargine + 0.015 mg/ml of polysorbate 20 | 0 | 0 | 0 | 0 |
| Insulin glargine + 0.020 mg/ml of polysorbate 20 | 0 | 0 | 0 | 0 |
| Insulin glargine + 0.030 mg/ml of polysorbate 20 | 0 | 0 | 0 | 0 |

| Test sample | Number of vials with particle formation after | | | |
|---|---|---|---|---|
| | 7 days | 14 days | 21 days | 28 days |
| Insulin glargine | 10 | 10 | 10 | 10 |
| Insulin glargine + 0.010 mg/ml of polysorbate 20 | 0 | 0 | 0 | 0 |
| Insulin glargine + 0.015 mg/ml of polysorbate 20 | 0 | 0 | 1 | 0 |
| Insulin glargine + 0.020 mg/ml of polysorbate 20 | 0 | 0 | 0 | 0 |
| Insulin glargine + 0.0030 mg/ml of polysorbate 20 | 1 | 1 | 1 | 1 |

Without addition of polysorbate 20, particle formation can occur in the solution even after 7 days in use. By addition of polysorbate 20, the particle formation can be markedly suppressed during the in use period.

The stabilizing action of polysorbate 20 is retained even on storage at elevated temperatures for a period of 3 months.

A decline in the stabilizing action due to possible hydrolysis of the polysorbate in the acidic medium of the solution cannot be determined in comparison with the data after storage for 1 month.

Example 2

Stabilization of Insulin Glargine Using Polysorbate 20 Under Physico-mechanical Stress Loading a) The solution is sterile-filtered through a combination of 0.2 μm und 0.1 μm filters. It is then poured into 10 ml injection vials and sealed using crimp caps having an inserted sealing disk.

b) A comparison solution is prepared identically, but first a suitable amount of surfactant (0.010-0.030 mg/ml of polysorbate 20) is suspended in water for injection.

The samples are stored at +5° C., 25° C. und 37° C. for a fixed period of time. 5 samples in each case are then subjected to a shaking test. The results are shown in the table below, the limit 15 FNU corresponds to turbidities which are discernible in daylight.

Storage for 1 month at 5° C.

| Test sample | Number of vials > 15 FNU | | | | | | | | |
|---|---|---|---|---|---|---|---|---|---|
| | 0 days | 0.5 days | 1 day | 2 days | 3 days | 4 days | 6 days | 8 days | 10 days |
| Insulin glargine | 0 | 0 | 0 | 2 | 3 | 3 | 4 | 4 | 4 |
| Insulin glargine + 0.010 mg/ml of polysorbate 20 | 0 | 0 | 0 | 0 | 0 | 1 | 3 | 4 | 5 |
| Insulin glargine + 0.015 mg/ml of polysorbate 20 | 0 | 0 | 0 | 0 | 0 | 0 | 0 | 0 | 0 |
| Insulin glargine + 0.020 mg/ml of polysorbate 20 | 0 | 0 | 0 | 0 | 0 | 0 | 0 | 0 | 0 |
| Insulin glargine + 0.030 mg/ml of polysorbate 20 | 0 | 0 | 0 | 0 | 0 | 0 | 0 | 0 | 0 |

Storage for 1 month at 25° C.

| Test sample | Number of vials > 15 FNU | | | | | | | | |
|---|---|---|---|---|---|---|---|---|---|
| | 0 days | 0.5 days | 1 day | 2 days | 3 days | 4 days | 6 days | 8 days | 10 days |
| Insulin glargine | 0 | 0 | 0 | 1 | 1 | 1 | 1 | 2 | 3 |
| Insulin glargine + 0.010 mg/ml of polysorbate 20 | 0 | 0 | 0 | 0 | 0 | 0 | 1 | 2 | 3 |
| Insulin glargine + 0.015 mg/ml of polysorbate 20 | 0 | 0 | 0 | 0 | 0 | 0 | 0 | 0 | 0 |
| Insulin glargine + 0.020 mg/ml of polysorbate 20 | 0 | 0 | 0 | 0 | 0 | 0 | 0 | 0 | 0 |
| Insulin glargine + 0.030 mg/ml of polysorbate 20 | 0 | 0 | 0 | 0 | 0 | 0 | 0 | 0 | 0 |

Storage for 1 month at 37° C.

| Test sample | Number of vials > 15 FNU | | | | | | | | |
|---|---|---|---|---|---|---|---|---|---|
| | 0 days | 0.5 days | 1 day | 2 days | 3 days | 4 days | 6 days | 8 days | 10 days |
| Insulin glargine | 0 | 0 | 0 | 2 | 5 | 5 | 5 | 5 | 5 |
| Insulin glargine + 0.010 mg/ml of polysorbate 20 | 0 | 0 | 0 | 0 | 0 | 0 | 0 | 0 | 0 |
| Insulin glargine + 0.015 mg/ml of polysorbate 20 | 0 | 0 | 0 | 0 | 0 | 0 | 0 | 0 | 0 |
| Insulin glargine + 0.020 mg/ml of polysorbate 20 | 0 | 0 | 0 | 0 | 0 | 0 | 0 | 0 | 0 |
| Insulin glargine + 0.030 mg/ml of polysorbate 20 | 0 | 0 | 0 | 0 | 0 | 0 | 0 | 0 | 0 |

Without addition of polysorbate 20, even after 2 days of severe physicomechanical stress, a visible turbidity can occur in the solution. By addition of polysorbate 20, the formation of turbidity during physicomechanical stressing can be markedly delayed. The stabilizing action of polysorbate 20 is retained even on storage at elevated temperatures.

A decline in the stabilizing action due to possible hydrolysis of the polysorbate in the acidic medium of the solution cannot be detected.

Example 3

Comparison of the Stabilization of the in Use Period of Insulin Glargine using Polysorbate 20 (Tween® 20) Und Using Polysorbate 80 (Tween® 20)

Open 10 vials in each case to give 5 ml of insulin glargine injection solution and
a) addition of 0.001 mg/ml of polysorbate 20
b) addition of 0.01 mg/ml of polysorbate 20
c) addition of 0.001 mg/ml of polysorbate 80
d) addition of 0.01 mg/ml of polysorbate 80 in the form of a concentrated stock solution.
The samples are then subjected to an in use test.
The results are shown in the table below.

| Test sample | Vials with particle formation after | | | |
|---|---|---|---|---|
| | 7 days | 14 days | 21 days | 28 days |
| Insulin glargine + 0.001 mg/ml of polysorbate 20 | no | yes | Yes, particles increasingly occur | Yes, particles increasingly occur |
| Insulin glargine + 0.010 mg/ml of polysorbate 20 | no | no | no | no |
| Insulin glargine + 0.001 mg/ml of polysorbate 80 | no | yes | Yes, particles increasingly occur | Yes, particles increasingly occur |
| Insulin glargine + 0.010 mg/ml of polysorbate 80 | no | no | no | no |

An addition of polysorbate 20 or of polysorbate 80 in a concentration of 0.001 mg/ml are equally able to stabilize the solution against particle formation during the in use period.

What is claimed is:

1. A pharmaceutical formulation comprising Gly(A21), Arg(B31), Arg(B32)-human insulin;
   at least one chemical entity chosen from esters and ethers of polyhydric alcohols;
   at least one preservative; and
   water,
   wherein the pharmaceutical formulation has a pH in the acidic range from 1 to 6.8.

2. The pharmaceutical formulation as claimed in claim 1, wherein the at least one preservative is chosen from phenols.

3. The pharmaceutical formulation as claimed in claim 1, wherein the at least one preservative is cresol.

4. The pharmaceutical formulation as claimed in claim 3, further including zinc.

5. The pharmaceutical formulation as claimed in claim 1, further including at least one isotonicizing agent.

6. The pharmaceutical formulation as claimed in claim 4, wherein the pharmaceutical formulation has a pH in the acidic range from 3.5 to 6.8.

7. The pharmaceutical formulation as claimed in claimed 6, wherein the pharmaceutical formulation has a pH in the acidic range from 3.5 to 4.5.

8. The pharmaceutical formulation as claimed in claim 1, wherein the at least one preservative is chosen from phenol, cresol, chlorocresol, benzyl alcohol, and parabens.

9. The pharmaceutical formulation as claimed in claim 5, wherein the at least one isotonicizing agent is chosen from mannitol, sorbitol, lactose, dextrose, trehalose, sodium chloride, and glycerol.

10. The pharmaceutical formulation as claimed in claim 1, further comprising a buffer.

11. The pharmaceutical formulation as claimed in claim 10, wherein the buffer is chosen from TRIS, phosphate, citrate, acetate, and glycylglycine.

12. The pharmaceutical formulation as claimed in claim 1, wherein the Gly(A21), Arg(B31), Arg(B32)-human insulin is present in a concentration of 60-6000 nmol/ml.

13. The pharmaceutical formulation as claimed in claim 12, wherein the Gly(A21), Arg(B31), Arg(B32)-human insulin is present in a concentration of 240-3000 nmol/ml.

14. The pharmaceutical formulation as claimed in claim 1, wherein the at least one chemical entity is present in a concentration of 5-200 µg/ml.

15. The pharmaceutical formulation as claimed in claim 14, wherein the at least one chemical entity is present in a concentration of 5-120 µg/ml.

16. The pharmaceutical formulation as claimed in claim 15, wherein the at least one chemical entity is present in a concentration of 20-75 µg/ml.

17. The pharmaceutical formulation as claimed in claim 9, wherein at least one isotonicizing agent is chosen from glycerol and mannitol and wherein said at least one isotonicizing agent is present in a concentration of 100-250 mM.

18. The pharmaceutical formulation as claimed in claim 1, further comprising one or more excipients chosen from acids, alkalis and salts.

19. The pharmaceutical formulation as claimed in claim 18, wherein the excipient is NaCl which is present in a concentration of up to 150 mM.

20. The pharmaceutical formulation as claimed in claim 10, wherein said buffer is present in a concentration of 5-250 mM.

* * * * *

UNITED STATES PATENT AND TRADEMARK OFFICE
CERTIFICATE OF CORRECTION

| | | |
|---|---|---|
| PATENT NO. | : 7,713,930 B2 | Page 1 of 1 |
| APPLICATION NO. | : 12/328208 | |
| DATED | : May 11, 2010 | |
| INVENTOR(S) | : Anette Brunner-Schwarz et al. | |

It is certified that error appears in the above-identified patent and that said Letters Patent is hereby corrected as shown below:

On Title Page 2, Item (56) under "Other Publications", line 1, delete "Glargin" and insert -- Glargine --, therefor.

In column 8, line 31, delete "mg/mlof" and insert -- mg/ml of --, therefor.

In column 8, line 34, delete "0.0030" and insert -- 0.030 --, therefor.

In column 11, line 35, delete "Und" and insert -- And --, therefor.

Signed and Sealed this
Thirty-first Day of May, 2011

David J. Kappos
*Director of the United States Patent and Trademark Office*

(12) INTER PARTES REVIEW CERTIFICATE (1862nd)
United States Patent
Brunner-Schwarz et al.

(10) Number: US 7,713,930 K1
(45) Certificate Issued: Jan. 5, 2021

(54) ACIDIC INSULIN PREPARATIONS HAVING IMPROVED STABILITY

(75) Inventors: Anette Brunner-Schwarz; Norbert Lill

(73) Assignee: SANOFI-AVENTIS DEUTSCHLAND GMBH

Trial Number:

IPR2017-01528 filed Jun. 5, 2017

Inter Partes Review Certificate for:

Patent No.: 7,713,930
Issued: May 11, 2010
Appl. No.: 12/328,208
Filed: Dec. 4, 2008

The results of IPR2017-01528 are reflected in this inter partes review certificate under 35 U.S.C. 318(b).

INTER PARTES REVIEW CERTIFICATE
U.S. Patent 7,713,930 K1
Trial No. IPR2017-01528
Certificate Issued Jan. 5, 2021

AS A RESULT OF THE INTER PARTES REVIEW PROCEEDING, IT HAS BEEN DETERMINED THAT:

Claims 1-20 are cancelled.

\* \* \* \* \*